(12) United States Patent
Kimura

(10) Patent No.: US 10,161,849 B2
(45) Date of Patent: Dec. 25, 2018

(54) CELL ANALYZER AND CELL ANALYZING METHOD

(71) Applicant: SYSMEX CORPORATION, Kobe-shi, Hyogo (JP)

(72) Inventor: Konobu Kimura, Kobe (JP)

(73) Assignee: SYSMEX CORPORATION, Kobe-shi (JP)

( * ) Notice: Subject to any disclaimer, the term of this patent is extended or adjusted under 35 U.S.C. 154(b) by 4 days.

(21) Appl. No.: 15/261,123

(22) Filed: Sep. 9, 2016

(65) Prior Publication Data
US 2017/0074777 A1    Mar. 16, 2017

(30) Foreign Application Priority Data

Sep. 11, 2015 (JP) ................................. 2015-179602

(51) Int. Cl.
G01N 15/14    (2006.01)
G01N 33/50    (2006.01)
(Continued)

(52) U.S. Cl.
CPC ....... *G01N 15/1436* (2013.01); *G01N 15/147* (2013.01); *G01N 15/1459* (2013.01);
(Continued)

(58) Field of Classification Search
CPC . G01N 15/1436; G01N 15/1459; G01N 21/53
(Continued)

(56) References Cited

U.S. PATENT DOCUMENTS 5,325,168 A * 6/1994 Nakamoto ......... G01N 15/1459
                                                              209/581
5,325,169 A * 6/1994 Nakamoto ......... G01N 15/1456
                                                              209/581
(Continued)

FOREIGN PATENT DOCUMENTS

EP    1542008 A1    6/2005
EP    1586903 A1    10/2005
(Continued)

OTHER PUBLICATIONS

Hiroyuki Takemura, Yoko Tabe, Kiyoshi Ishii, Yuki Kobayashi, Yutaka Kuno, Takashi Horii, Kazunori Miyake, Takashi Miida and Akimichi Ohsaka, "Evaluation of Capability of Cell Count and Detection of Tumor Cells in Cerebrospinal and Body Fluids by Automated Hematology Analyzer", Rinsho Byori, 2010. 559-564, 58:6.

*Primary Examiner* — Roy M Punnoose
(74) *Attorney, Agent, or Firm* — Metrolexis Law Group, PLLC

(57) ABSTRACT

Disclosed is a cell analyzer that includes a flow cell through which a measurement specimen containing a body fluid flows, a light emission unit that applies light onto the measurement specimen flowing through the flow cell, a light detection unit that detects forward scattered light generated from cells in the measurement specimen to which the light is applied, an analysis unit that is programmed to analyze the cells in the body fluid based on a forward scattered light signal detected by the light detection unit, and an output unit. The analysis unit is programmed to control the output unit to output information about tumor cells in the body fluid, based on forward scattered light signal intensity and forward scattered light signal width.

8 Claims, 12 Drawing Sheets

(51) Int. Cl.
  *G01N 15/00* (2006.01)
  *G01N 21/47* (2006.01)
  *G01N 21/64* (2006.01)

(52) U.S. Cl.
  CPC ..... *G01N 21/6428* (2013.01); *G01N 33/5094*
    (2013.01); *G01N 2015/0065* (2013.01); *G01N*
    *2015/1402* (2013.01); *G01N 2015/1477*
    (2013.01); *G01N 2015/1486* (2013.01); *G01N*
    *2015/1488* (2013.01); *G01N 2021/4704*
    (2013.01); *G01N 2021/4726* (2013.01); *G01N*
    *2021/6439* (2013.01); *G01N 2021/6482*
    (2013.01)

(58) Field of Classification Search
  USPC .......................................................... 356/338
  See application file for complete search history.

(56) References Cited

U.S. PATENT DOCUMENTS

| | | | | |
|---|---|---|---|---|
| 5,693,484 A * | 12/1997 | Nakamoto | ............... | C12Q 1/68 209/581 |
| 5,731,867 A * | 3/1998 | Katayama | .......... | G01N 15/1456 356/318 |
| 5,888,823 A * | 3/1999 | Matsumoto | ........ | G01N 15/1012 436/10 |
| 5,891,733 A * | 4/1999 | Inoue | ..................... | G01N 15/12 436/10 |
| 6,005,256 A * | 12/1999 | McGlynn | ........... | G01N 21/6428 250/461.2 |
| 6,118,522 A * | 9/2000 | Kanai | ................ | G01N 15/1429 356/336 |
| 6,133,995 A * | 10/2000 | Kubota | .............. | G01N 15/1459 356/337 |
| 6,165,740 A * | 12/2000 | Fukuda | .................... | C12Q 1/04 435/283.1 |
| 6,514,722 B2 * | 2/2003 | Palsson | .................. | C12M 35/02 435/29 |
| 6,534,308 B1 * | 3/2003 | Palsson | .................. | C12M 35/02 382/133 |
| 7,625,730 B2 * | 12/2009 | Tsuji | ...................... | G01N 33/52 435/173.9 |
| 7,923,229 B2 * | 4/2011 | Tsuji | ...................... | G01N 33/52 435/173.9 |
| 8,218,840 B2 * | 7/2012 | Eisfeld | ............... | G06K 9/00127 359/368 |
| 9,733,186 B2 * | 8/2017 | Ishisaka | ............. | G01N 21/6486 |
| 9,784,729 B2 * | 10/2017 | Ebi | ..................... | G01N 33/5091 |
| 9,945,783 B2 * | 4/2018 | Ebi | ..................... | G01N 21/6486 |
| 2005/0202400 A1 * | 9/2005 | Tsuji | ...................... | G01N 33/52 435/4 |
| 2008/0176274 A1 * | 7/2008 | Tsuji | ...................... | G01N 33/52 435/34 |
| 2008/0187951 A1 * | 8/2008 | Nagai | .................... | G01N 15/12 435/29 |
| 2013/0280729 A1 * | 10/2013 | Ebi | .................... | G01N 15/1475 435/6.14 |
| 2013/0280730 A1 * | 10/2013 | Ebi | ...................... | G01N 15/147 435/6.14 |
| 2014/0199702 A1 * | 7/2014 | Ebi | ...................... | C12Q 1/6886 435/6.14 |
| 2016/0054222 A1 * | 2/2016 | Tateyama | ............. | G01N 33/493 435/34 |
| 2017/0322159 A1 * | 11/2017 | Ishisaka | ............. | G01N 21/6486 |

FOREIGN PATENT DOCUMENTS

| | | |
|---|---|---|
| EP | 2204643 A1 | 7/2010 |
| EP | 2645082 A2 | 10/2013 |
| EP | 2645083 A2 | 10/2013 |
| EP | 2645082 A3 | 12/2013 |
| EP | 2645083 A3 | 12/2013 |
| JP | 2002-207035 A | 7/2002 |
| JP | 2008-209386 A | 9/2008 |

\* cited by examiner

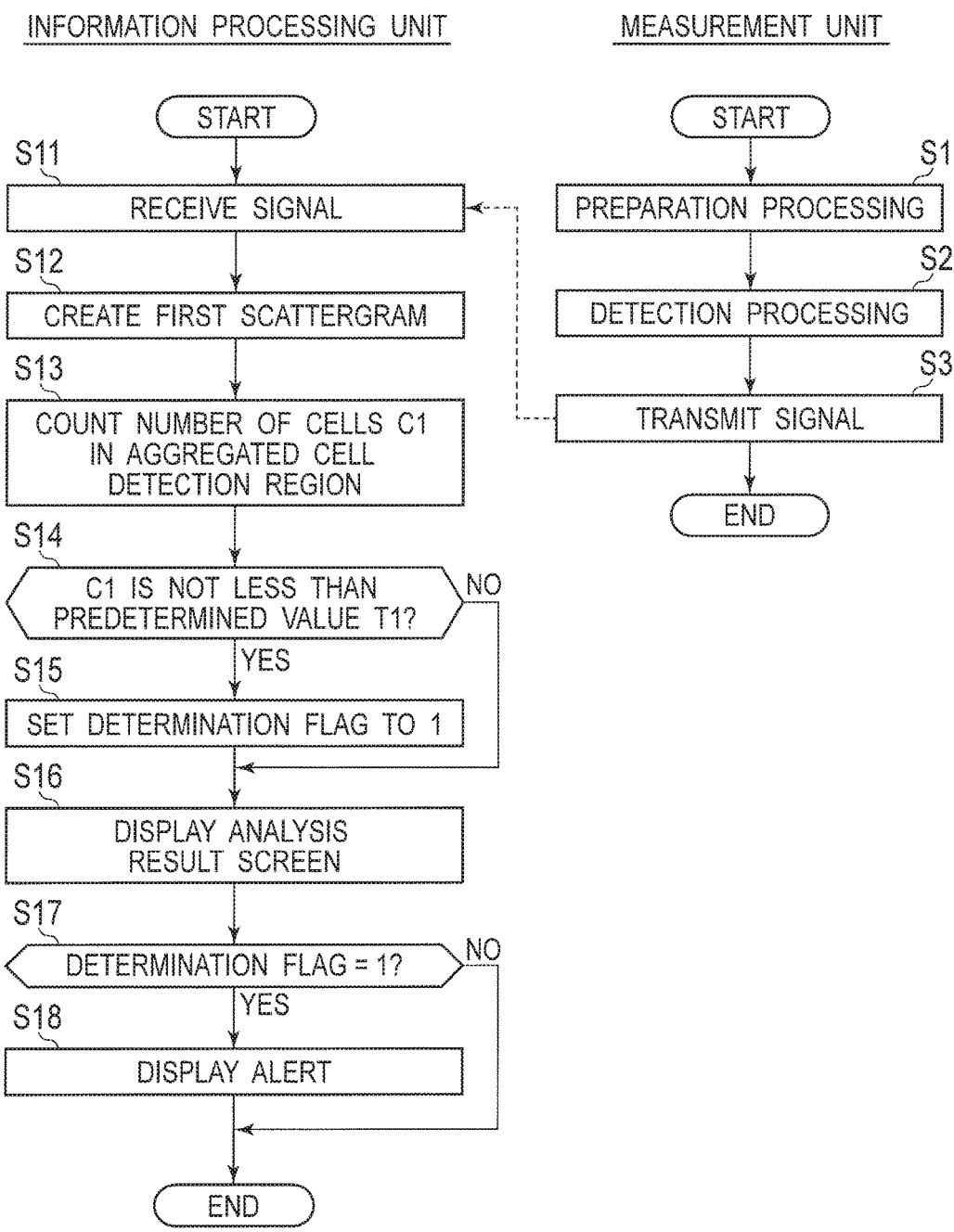

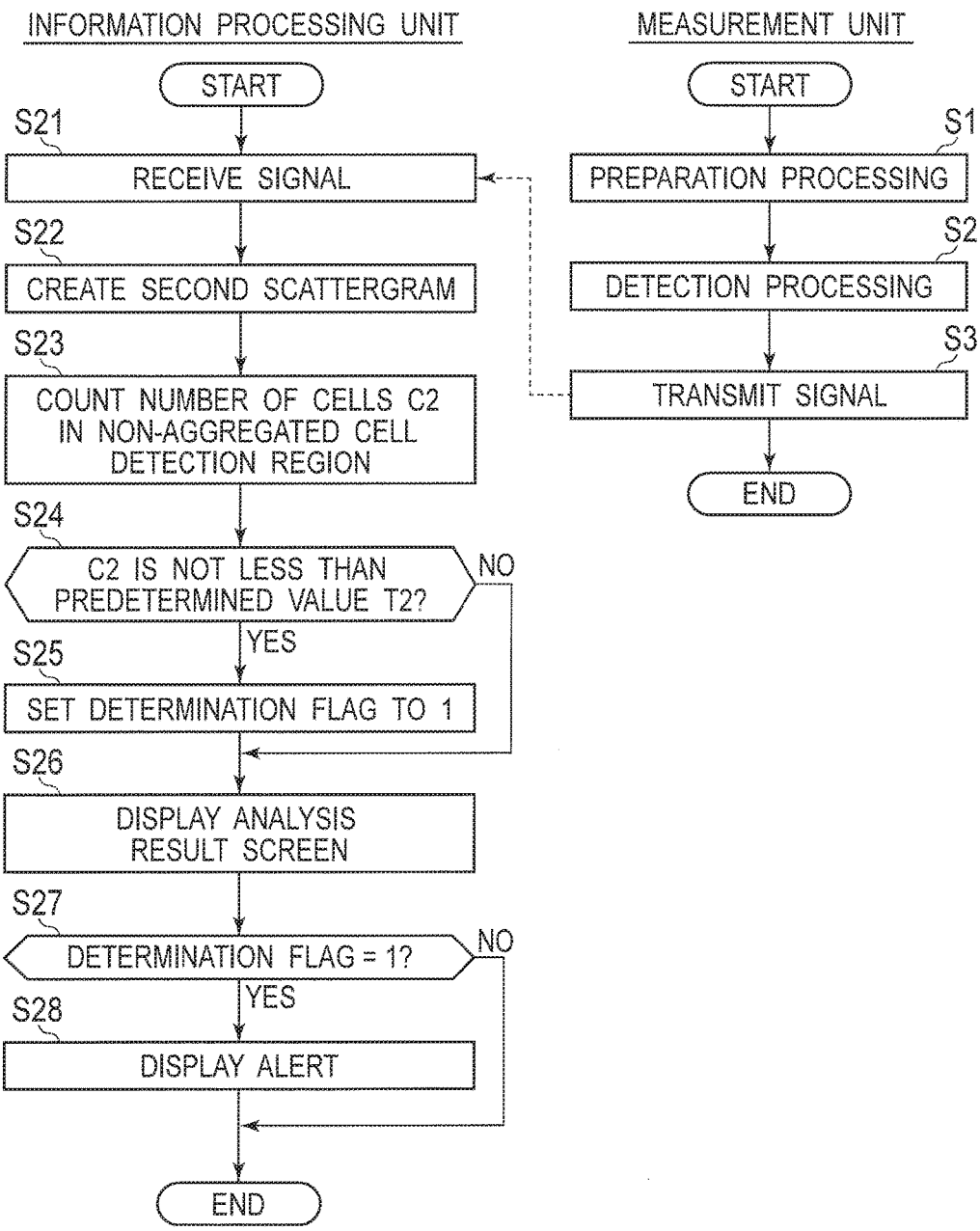

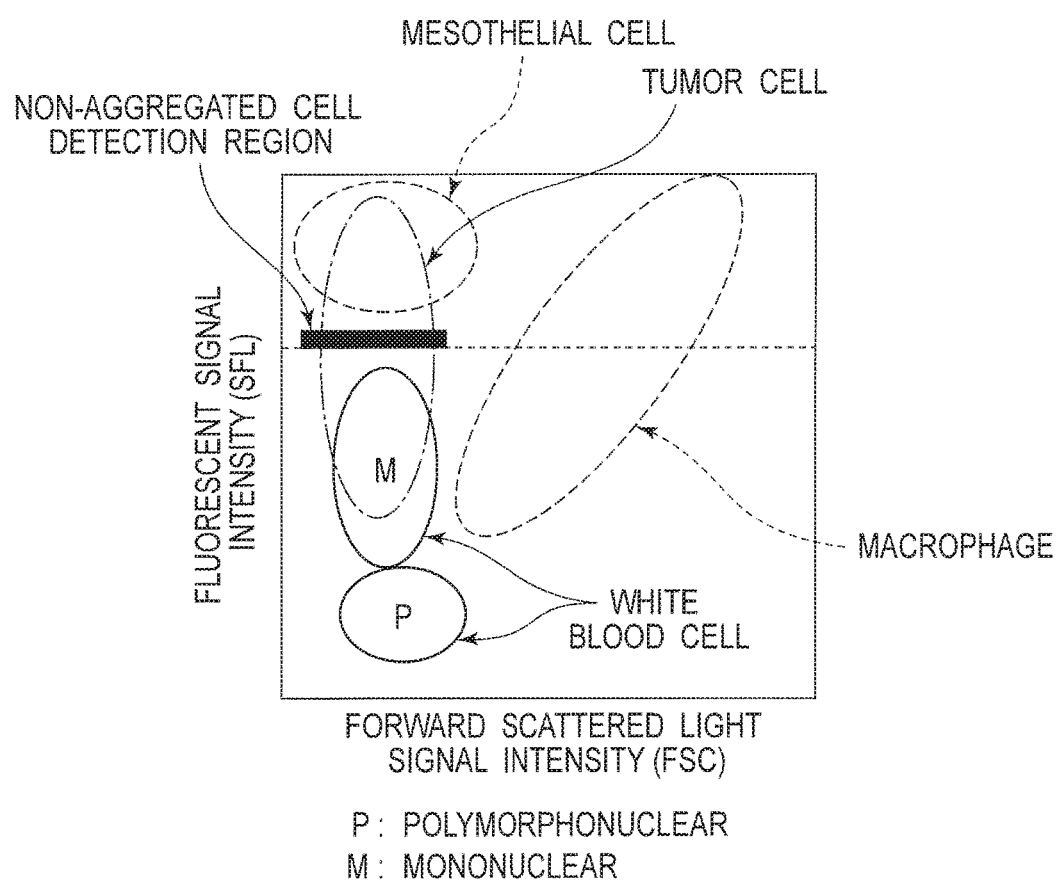

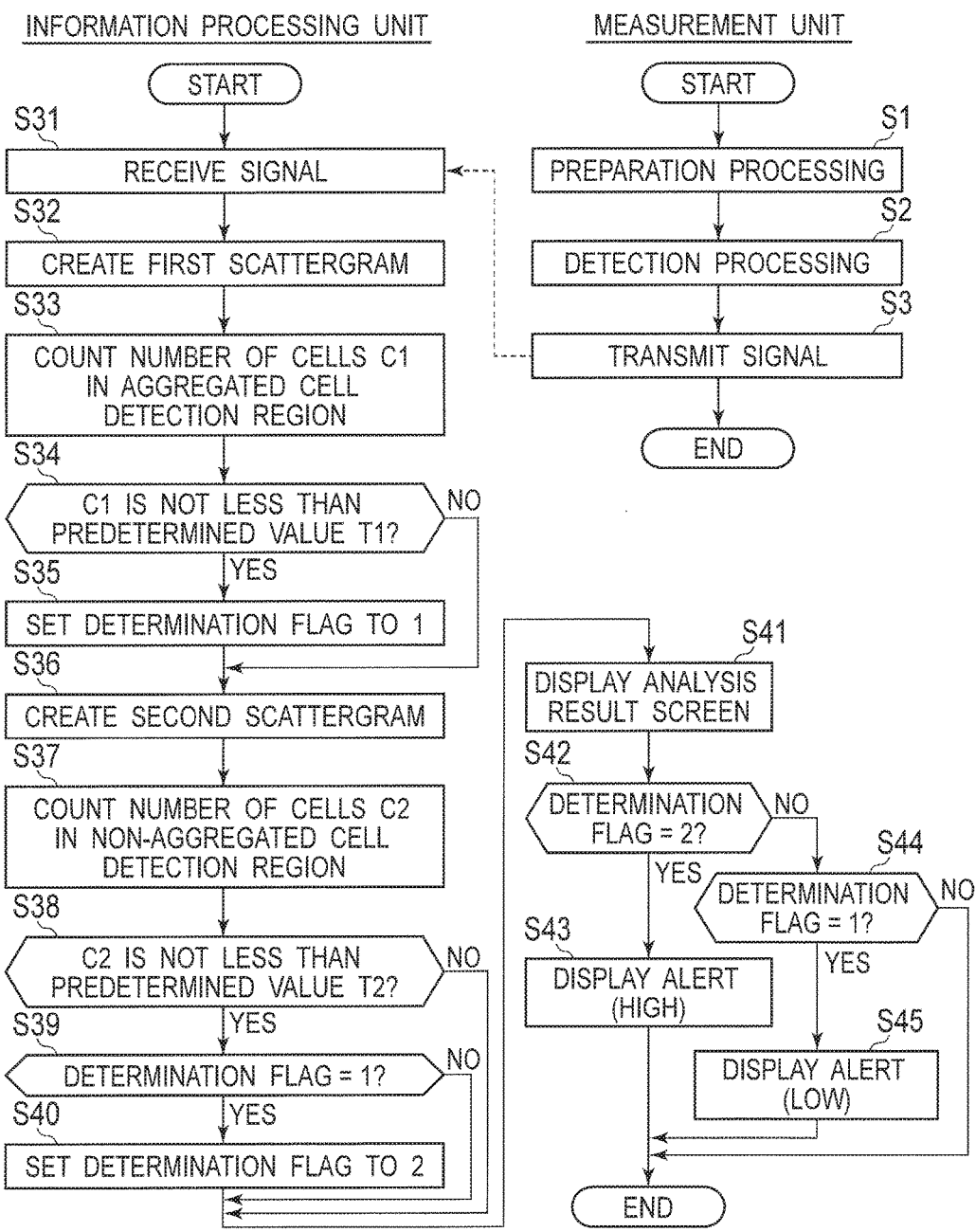

CELL ANALYZER AND CELL ANALYZING METHOD

CROSS REFERENCE TO RELATED APPLICATIONS

This application claims priority to prior Japanese Patent Application No. 2015-179602 filed on Sep. 11, 2015 entitled "CELL ANALYZER AND CELL ANALYZING METHOD" the entire contents of which are hereby incorporated by reference.

BACKGROUND

The disclosure relates to a cell analyzer and a cell analyzing method. More particularly, the disclosure relates to a cell analyzer and a cell analyzing method for analyzing cells in a body fluid such as a cerebrospinal fluid and a coelomic fluid.

Analysis of a body fluid of a patient has heretofore been conducted to diagnose a disease. For example, US2008/0187951A discloses a blood cell analyzer and a body fluid analyzing method for obtaining information on white blood cells in blood. In the method described in US2008/0187951A, white blood cells in a body fluid are analyzed separately from non-target particles such as macrophages, mesothelial cells, and tumor cells, which are particles other than the white blood cells. In a scattergram with side fluorescence intensity as the vertical axis and side scattered light intensity as the horizontal axis, a region where the white blood cells are to appear is set to a region excluding a high fluorescence intensity region where the non-target particles are present, and excluding a low fluorescence intensity region where red blood cell ghosts generated by hemolysis are distributed.

SUMMARY

US2008/0187951A states that the body fluid contains tumor cells as the non-target particles. However, the technique in US2008/0187951A cannot determine whether the non-target particles appearing in the body fluid are macrophages, mesothelial cells, or tumor cells, and therefore cannot detect tumor cells contained in the body fluid.

(1) A cell analyzer according to a first aspect of embodiments includes: a flow cell through which a measurement specimen containing a body fluid flows; a light emission unit that applies light onto the measurement specimen flowing through the flow cell; a light detection unit that detects forward scattered light generated from cells in the measurement specimen to which the light is applied; an analysis unit that is programmed to analyze the cells in the body fluid based on a forward scattered light signal detected by the light detection unit; and an output unit, wherein the analysis unit is programmed to control the output unit to output information about tumor cells in the body fluid, based on forward scattered light signal intensity and forward scattered light signal width.

(2) A cell analyzer according to a second aspect of embodiments includes: a flow cell through which a measurement specimen flows, the measurement specimen being obtained by fluorescently staining nucleic acids of nucleated cells in a body fluid; a light emission unit that applies light onto the measurement specimen flowing through the flow cell; a light detection unit that detects fluorescence generated from cells in the measurement specimen to which the light is applied; an analysis unit that is programmed to analyze cells in the body fluid based on fluorescent signal intensity detected by the light detection unit; and an output unit, wherein the analysis unit is programmed to control the output unit to output information about tumor cells in the body fluid, based on the fluorescent signal intensity and forward scattered light signal intensity.

(3) A cell analyzing method according to a third aspect of embodiments includes: applying light to a measurement specimen containing a body fluid; detecting forward scattered light generated from cells in the measurement specimen to which the light is applied; and outputting information about tumor cells in the body fluid based on forward scattered light signal intensity and forward scattered light signal width.

(4) A cell analyzing method according to a fourth aspect of embodiments includes: preparing a measurement specimen by fluorescently staining nucleic acids of nucleated cells in a body fluid; applying light to the measurement specimen; detecting fluorescence generated from cells in the measurement specimen; and outputting information about tumor cells in the body fluid based on fluorescent signal intensity and forward scattered light signal intensity.

(5) A cell analyzing method according to a fifth aspect of embodiments includes: applying light to a measurement specimen containing a body fluid; detecting light generated from cells in the measurement specimen to which the light is applied; counting the number of tumor cells separately from at least white blood cells, macrophages, and mesothelial cells, based on cell distribution information generated from the detected light information; and outputting information about tumor cells in the body fluid.

BRIEF DESCRIPTION OF DRAWINGS

FIG. 8 is a flowchart illustrating processing by the measurement unit and the information processing unit in a cell analyzing method according to a first embodiment.

FIG. 10 is a flowchart illustrating processing by the measurement unit and the information processing unit in a cell analyzing method according to a second embodiment.

FIG. 11 is a schematic view of a scattergram used in the cell analyzing method according to the second embodiment.

FIG. 12 is a flowchart illustrating processing by the measurement unit and the information processing unit in a cell analyzing method according to a third embodiment.

EMBODIMENTS

Hereinafter, with reference to the accompanying drawings, detailed description is given of embodiments of a cell analyzer and a cell analyzing method. Note that the invention is not limited to these examples but is defined by the scope of the claims, and is intended to include meanings equivalent to the scope of the claims and all modifications within the scope.

[Cell Analyzer]

Figure 1:
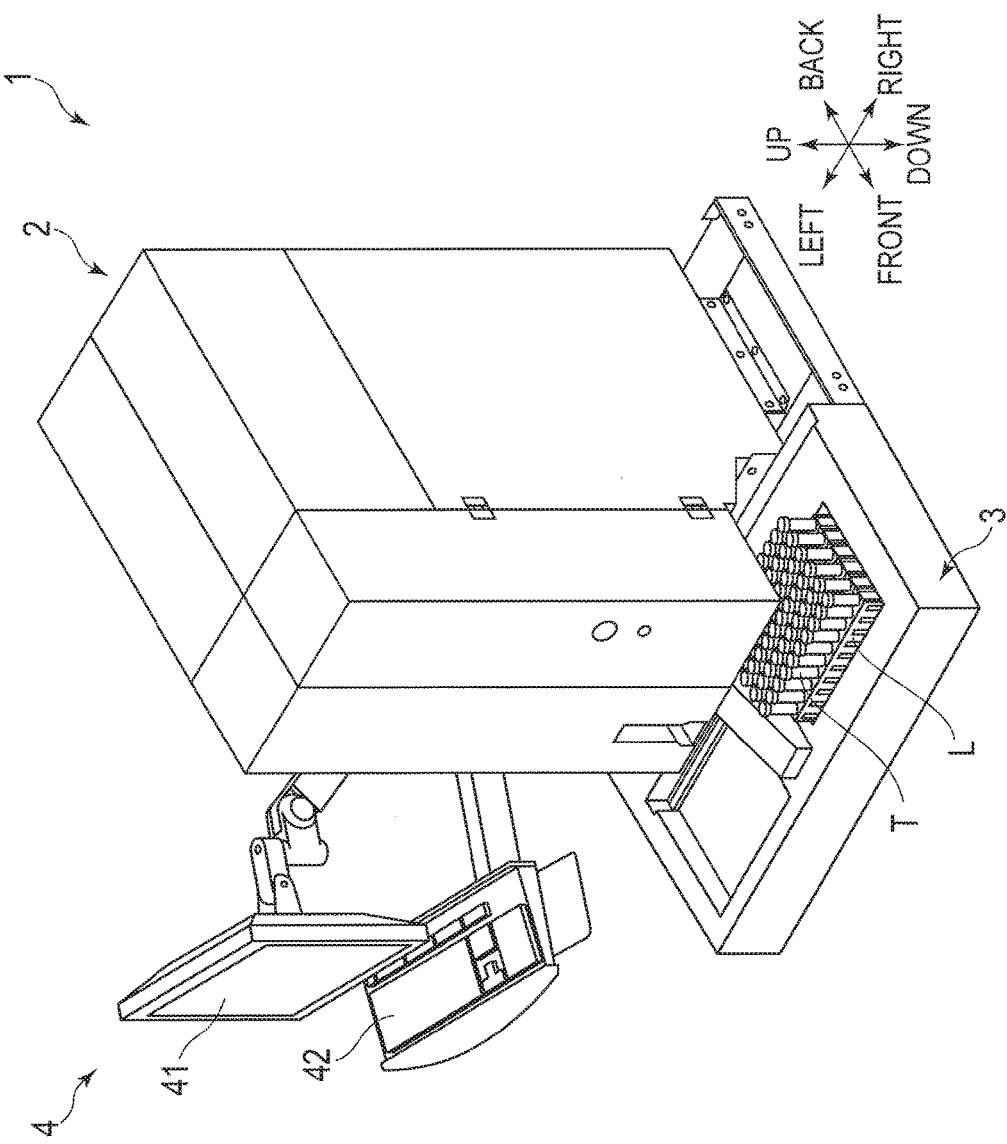
FIG. 1 is a perspective view illustrating an external appearance of a cell analyzer of an embodiment.

Cell analyzer 1 according to this embodiment is a cell analyzer for detecting nucleated cells such as white blood cells, macrophages, mesothelial cells, and tumor cells, which are contained in a body fluid sample, and for counting the numbers of the respective cells. Note that the "body fluid" in embodiments means cerebrospinal fluid, ascites, pleural effusion, synovial fluid, peritoneal dialysis fluid, and the like except blood. As illustrated in FIG. 1, cell analyzer 1 includes measurement unit 2, transport unit 3 disposed on the front side of measurement unit 2, and information processing unit 4. A body fluid sample collected from a patient is stored in sample container T. Multiple sample containers T are supported on sample rack L. Sample rack L is transported by transport unit 3, thereby supplying the body fluid sample to measurement unit 2.

Information processing unit 4 includes output unit 41 and input unit 42. Information processing unit 4 is communicably connected to measurement unit 2, transport unit 3, and host computer 5 (see FIG. 2). Information processing unit 4 controls operations of measurement unit 2 and transport unit 3, conducts analysis based on the result of measurement performed by measurement unit 2, and transmits the result of the analysis to host computer 5.

Figure 2:
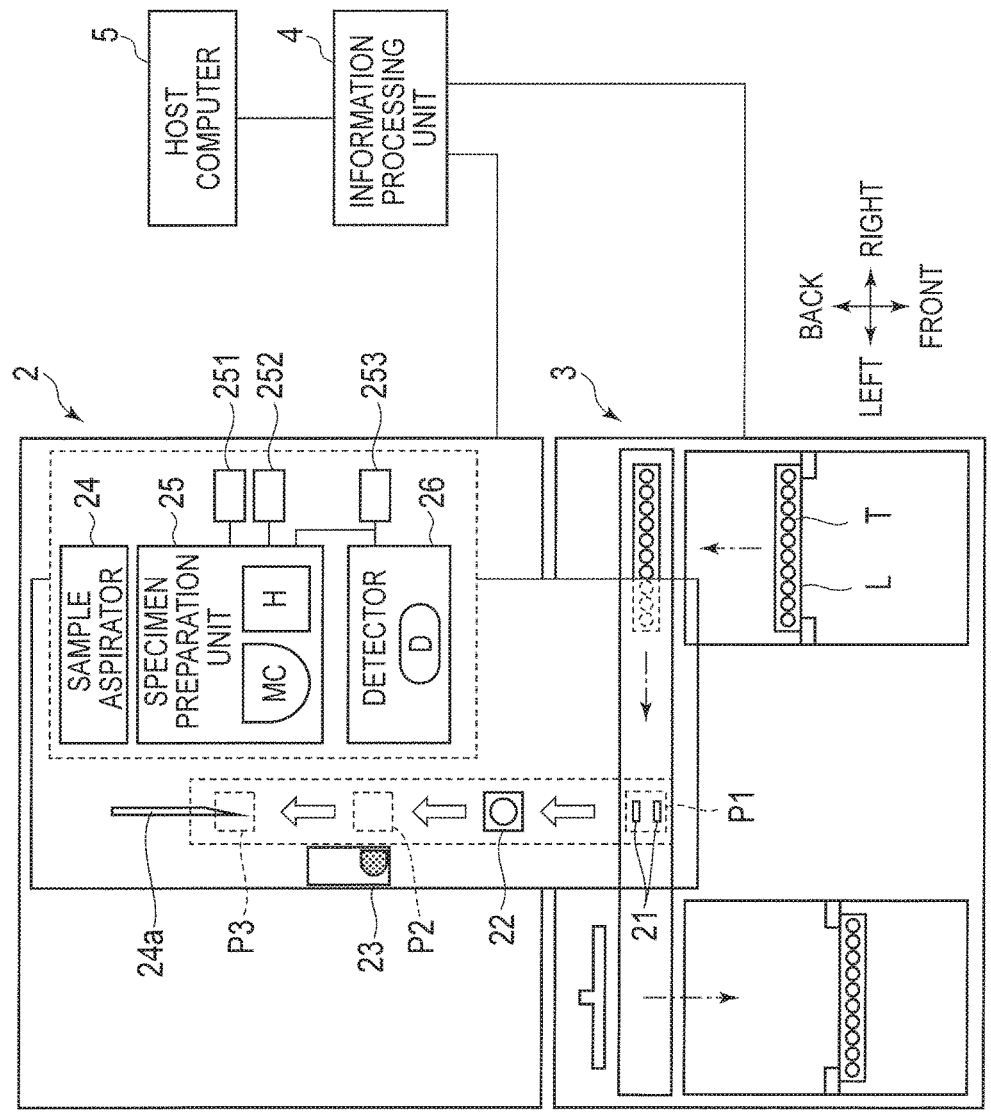
FIG. 2 is a schematic view illustrating a configuration of a measurement unit in the cell analyzer illustrated in FIG. 1.

As illustrated in FIG. 2, measurement unit 2 includes hand unit 21, sample container setting unit 22, bar code unit 23, sample aspirator 24, specimen preparation unit 25, and detector 26. Sample aspirator 24 includes piercer 24a to aspirate the sample from sample container T. Specimen preparation unit 25 includes mixing chamber MC and heater H, and prepares a measurement specimen to be used for measurement by mixing a reagent into the sample. Detector 26 includes optical detector D to detect cells from the measurement specimen. Each of the components in measurement unit 2 is controlled by information processing unit 4.

Sample container T located at position P1 by transport unit 3 is held by hand unit 21 and taken upward out of sample rack L. The sample in sample container T is agitated by swinging hand unit 21. Then, hand unit 21 sets sample container T finished with the agitation in sample container setting unit 22 located at position P1. Thereafter, sample container T is transported to position P2 by sample container setting unit 22.

Once sample container T is located at position P2, bar code unit 23 provided near position P2 reads a sample number from a bar code label attached to sample container T. Then, sample container T is transported to position P3 by sample container setting unit 22. Once sample container T is located at position P3, sample aspirator 24 aspirates a predetermined amount of sample from sample container T through piercer 24a. Upon completion of the aspiration of the sample, sample container T is transported forward by sample container setting unit 22 and returned to the original support position on sample rack L by the hand unit 21. As to the sample aspirated through piercer 24a, a predetermined amount thereof is discharged into mixing chamber MC by sample aspirator 24 after piercer 24a is transferred to the position of mixing chamber MC.

Specimen preparation unit 25 is connected to reagent container 251 for storing a first reagent, reagent container 252 for storing a second reagent, and reagent container 253 for storing a sheath liquid (diluted solution) through tubes. Specimen preparation unit 25 is connected to a compressor (not illustrated) and can take the reagents from sample containers 251 to 253, respectively, by pressure generated by the compressor. Specimen preparation unit 25 prepares the measurement specimen by mixing the body fluid sample, the first reagent, and the second reagent in mixing chamber MC and heating the mixed liquid with heater H for a predetermined period of time. The measurement specimen prepared by specimen preparation unit 25 is supplied to optical detector D in detector 26.

Detector 26 is connected to reagent container 253 for storing the sheath liquid (diluted solution) through a tube. Detector 26 is connected to a compressor (not illustrated) and can take the sheath liquid (diluted solution) from reagent container 253 by pressure generated by the compressor.

Figure 3:
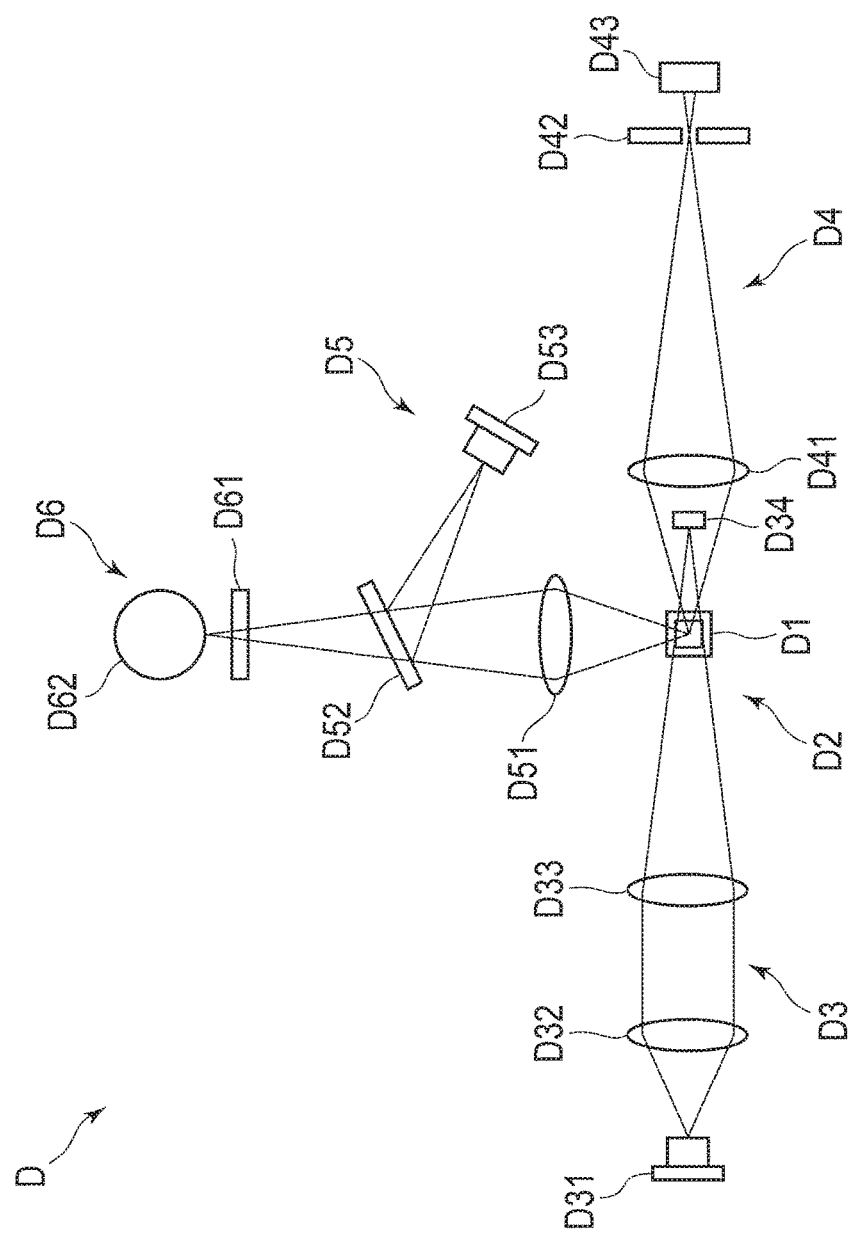
FIG. 3 is a schematic view illustrating a configuration of an optical detector in the cell analyzer illustrated in FIG. 1.

As illustrated in FIG. 3, optical detector D includes flow cell D1, sheath flow system D2, beam spot formation system D3, forward scattered light reception system D4, side scattered light reception system D5, and fluorescence reception system D6.

Sheath flow system D2 generates a liquid flow in flow cell D1 by sending the measurement specimen in a state of being enclosed in the sheath liquid into flow cell D1. Beam spot formation system D3 is configured such that light emitted from semiconductor laser D31 that is a light emission unit is applied to flow cell D1 after passing through collimator lens D32 and condenser lens D33. Thus, laser beams are applied to cells included in the liquid flow passing through flow cell D1. Beam spot formation system D3 also includes beam stopper D34.

Forward scattered light reception system D4 is configured such that front condenser lens D41 collects light scattered forward (forward scattered light) and photodiode D43 receives light passing through pinhole D42. Photodiode D43 outputs a forward scattered light signal (FSC) based on a peak value of the received forward scattered light. Side scattered light reception system D5 is configured such that side condenser lens D51 collects light scattered to the side (side scattered light) and part of the light is reflected by dichroic mirror D52 and received by photodiode D53. Photodiode D53 outputs a side scattered light signal (SSC) based on a peak value of the received side scattered light.

Light scattering is a phenomenon that occurs when there is a particle such as a cell in a traveling direction of light as an obstacle and the particle changes the traveling direction of light. Information about the size and material of the particle can be obtained by detecting the scattered light. Particularly, information about the size of the particle (cell) can be obtained from forward scattered light. Meanwhile, information about the inside of the particle can be obtained from side scattered light. When a laser beam is applied to the cell, side scattered light intensity depends on the complexity (shape, size, and density of a nucleus, and an amount of granules) in the cell.

Fluorescence reception system D6 is configured such that light (fluorescence) transmitted through dichroic mirror D52 among the side scattered light further passes through spectral filter D61 and is received by avalanche photodiode D62. Avalanche photodiode D62 outputs a fluorescent signal (SFL) based on a peak value of the received fluorescence.

When light is applied to a cell stained with a fluorescent material, fluorescence having a wavelength longer than that of the applied light is generated. The intensity of the fluorescence is high when the cell is stained well. Information about how well the cell is stained can be obtained by measuring the fluorescence intensity.

In this embodiment, photodiode D43, photodiode D53, and avalanche photodiode D62 constitute a light detection unit.

Referring back to FIG. 2, the forward scattered light signal, the side scattered light signal, and the fluorescent signal acquired by optical detector D are transmitted to information processing unit 4. Information processing unit 4 executes analysis based on the received signals.

Figure 4:
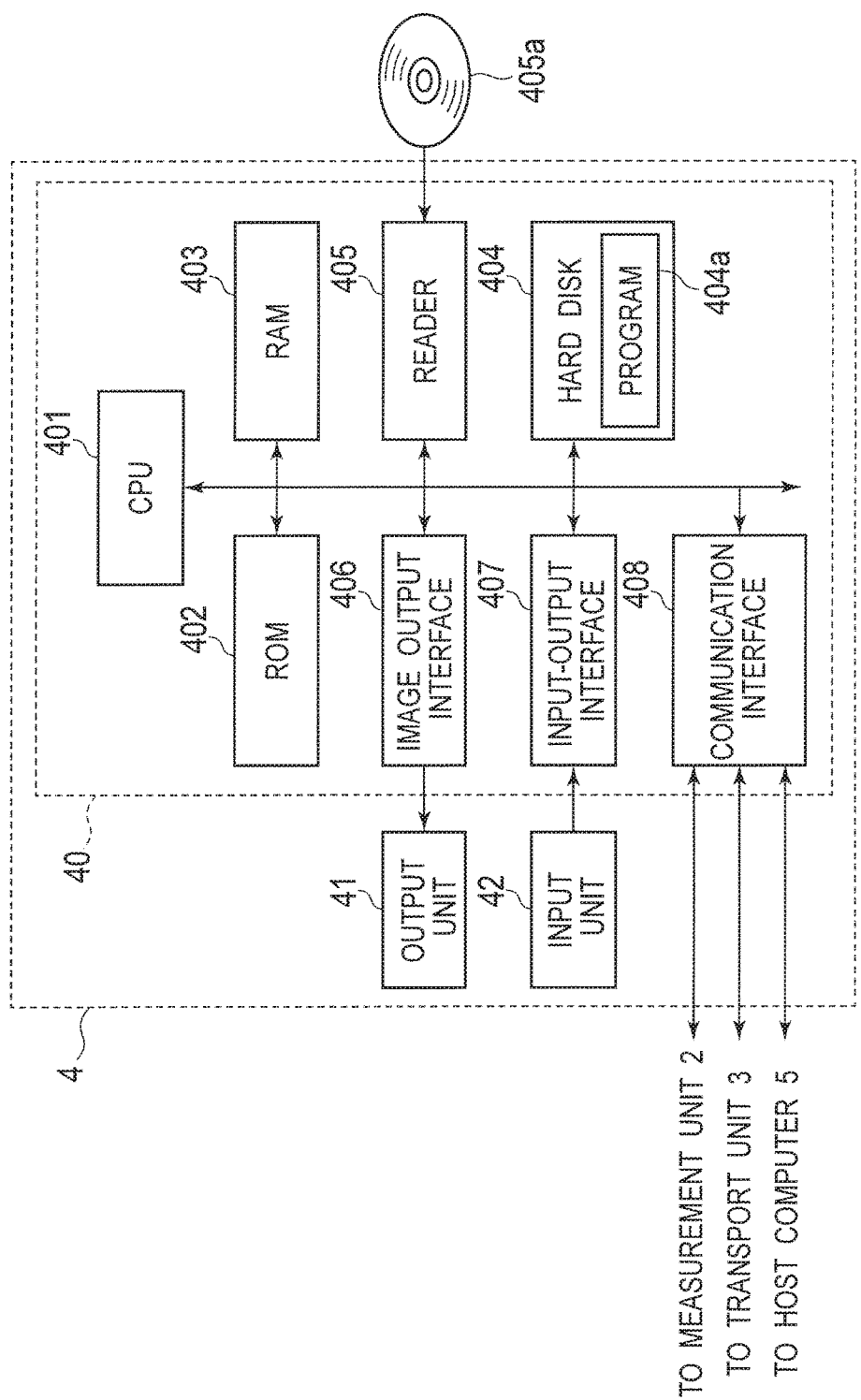
FIG. 4 is an explanatory diagram illustrating a configuration of an information processing unit in the cell analyzer illustrated in FIG. 1.

As illustrated in FIG. 4, information processing unit 4 is a personal computer, and includes main body 40, output unit 41, and input unit 42. Main body 40 includes CPU 401, ROM 402, RAM 403, hard disk 404, reader 405, image output interface 406, input-output interface 407, and communication interface 408. Output unit 41 in this embodiment is a display capable of displaying images and the like. Alternatively, a printer which outputs information on paper or the like can also be adopted as the output unit.

CPU 401 included in an analysis unit executes a computer program stored in ROM 402 and a computer program loaded into RAM 403. RAM 403 is used to read computer programs stored in ROM 402 and hard disk 404. RAM 403 is also used as a work area for CPU 401 to execute the computer programs.

Hard disk 404 stores an operating system, computer programs to be executed by CPU 401, and data used to execute the computer programs. Hard disk 404 stores program 404a for information processing unit 4 to execute processing illustrated in FIGS. 8, 10, and 12. Reader 405 includes a CD drive, a DVD drive or the like, and can read computer programs and data stored in storage medium 405a. When program 404a is stored in storage medium 405a, program 404a read from storage medium 405a by reader 405 is stored in hard disk 404.

Image output interface 406 outputs a video signal corresponding to image data to output unit 41. Output unit 41 displays images based on the video signal outputted from image output interface 406. A user inputs an instruction through input unit 42. Input-output interface 407 receives a signal inputted through input unit 42. Communication interface 408 is connected to measurement unit 2, transport unit 3, and host computer 5. CPU 401 transmits and receives instruction signals and data to and from these devices through communication interface 408.

Specimen preparation unit 25 prepares a measurement specimen by mixing a body fluid sample with a reagent, in order to stain nucleic acids of a cell (nucleated cell) by hemolyzing red blood cells that may be contained in a body fluid and damaging cell membranes of cells such as white bloods cell to the extent that fluorescent dye can permeate the cell membranes of the cells. To be more specific, the measurement specimen is prepared by mixing the following first reagent and second reagent with the body fluid sample.

The first reagent contains fluorescent dye capable of staining nucleic acids of a nucleated cell, for fluorescently staining nucleic acids of a nucleated cell in a body fluid specimen treated with the second reagent to be described later. A cell such as a white blood cell having nucleic acids is stained by treating a blood specimen with the first reagent.

The fluorescent dye is not particularly limited as long as the dye can stain the nucleic acids, and can be appropriately selected according to the wavelength of light emitted from a light source (semiconductor laser D31). Examples of such a fluorescent dye include propidium iodide, ethidium bromide, ethidium-acridine heterodimer, ethidium diazide, ethidium homodimer-1, ethidium homodimer-2, ethidium monoazide, trimethylene bis [[3-[[4-[[(3-methylbenzothiazole-3-ium)-2-il]methylene]-1,4-dihydroquinoline]-1-il]propyl]dimethylaminium].tetraiodide (TOTO-1), 4-[(3-methylbenzothiazole-2(3H)-ylidene)methyl]-1-[3-(trimethylaminio)propyl]quinolinium.diiodide (TO-PRO-1), N,N,N',N'-tetramethyl-N,N'-bis [3-[4-[3-[(3-methylbenzothiazole-3-ium)-2-il]-2-propenylidene]-1,4-dihydroquinoline-1-il]propyl]-1,3-propanediaminium-tetraiodide (TOTO-3) or 2-[3-[[1-[3-(trimethylaminio)propyl]-1,4-dihydroquinoline]-4-ylidene]-1-propenyl]-3-methylbenzothiazole-3-ium-diiodide (TO-PRO-3) and fluorescent dye represented by the following general formula (I). Among the above, the fluorescent dye represented by following general formula (I) is preferable.

[Formula 1]

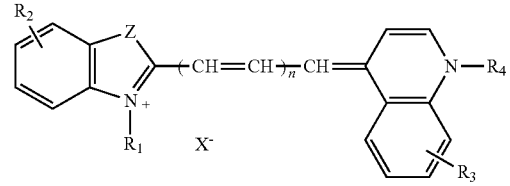

(I)

In formula (I), $R_1$ and $R_4$ are the same or different from each other and are a hydrogen atom, an alkyl group, an alkyl chain having a hydroxyl group, an alkyl chain having an ether group, an alkyl chain having an ester group or a benzyl group that may have a substituent. $R_2$ and $R_3$ are the same or different from each other and are a hydrogen atom, a hydroxyl group, a halogen, an alkyl group, an alkenyl group, an alkynyl group, an alkoxy group, an alkylsulphonyl group or a phenyl group. Z is a sulphur atom, an oxygen atom or a carbon atom having a methyl group. n is 0, 1, 2 or 3, and $X^-$ is an anion.

In this embodiment, the alkyl group may be linear or branched. In formula (I), it is preferable that, when one of $R_1$ and $R_4$ is an alkyl group having 6 to 18 carbon atoms, the other is a hydrogen atom or an alkyl group having less than 6 carbon atoms. Among the alkyl groups having 6 to 18 carbon atoms, the alkyl group having 6, 8 or 10 carbon atoms is preferable.

In formula (I), the substituent of the benzyl group in $R_1$ and $R_4$ may include, for example, alkyl groups having 1 to 20 carbon atoms, alkenyl groups having 2 to 20 carbon atoms, and alkynyl groups having 2 to 20 carbon atoms. Among these, a methyl or ethyl group is particularly preferable.

In formula (I), the alkenyl group in $R_2$ and $R_3$ may include, for example, alkenyl groups having 2 to 20 carbon atoms. The alkoxy group in $R_2$ and $R_3$ may include alkoxy groups having 1 to 20 carbon atoms. Among these, a methoxy or ethoxy group is particularly preferable.

In formula (I), the anion $X^-$ may include halogen ions such as $F^-$, $Cl^-$, $Br^-$ and $I^-$, $CF_3SO_3^-$, $BF_4^-$, and the like.

The first reagent may contain one or two or more types of fluorescent dyes.

The concentration of the fluorescent dye in the first reagent can be appropriately set depending on the type of the fluorescent dye, and is usually 0.01 to 100 pg/μL, preferably 0.1 to 10 pg/μL. When the fluorescent dye represented by formula (I) is used as the fluorescent dye in the first reagent, for example, the concentration of the fluorescent dye in the first reagent is preferably 0.2 to 0.6 pg/μL, more preferably 0.3 to 0.5 pg/μL.

The first reagent can be obtained by dissolving the fluorescent dye in a suitable solvent so as to obtain the concentration described above. The solvent is not particularly limited as long as the solvent can dissolve the fluorescent dye described above, and may include water, organic solvents, and mixtures thereof, for example. The organic solvents may include, for example, alcohols, ethylene glycol, dimethyl sulphoxide (DMSO), and the like. The fluorescent dye is preferably dissolved in an organic solvent because the dye may have poor storage stability in aqueous solutions.

The first reagent may be a commercial staining reagent for classifying white blood cells. Such a staining reagent may include, for example, Fluorocell (registered trademark) WDF manufactured by Sysmex Corporation. Fluorocell WDF is a staining reagent containing the fluorescent dye represented by formula (I).

The second reagent contains surfactants, i.e., cationic surfactants and/or nonionic surfactants, for damaging cell membranes of cells to the extent that the fluorescent dye in the first reagent can permeate the cell membranes of the cells. The second reagent further contains an aromatic organic acid at a concentration of 20 mM to 50 mM. Here, when the second reagent contains the aromatic organic acid at a concentration of 20 mM to 30 mM, the second reagent has pH of 5.5 to 6.4. When the second reagent contains the aromatic organic acid at a concentration of 30 mM to 50 mM, the second reagent has pH of 5.5 to 7.0.

In this embodiment, when the second reagent contains the aromatic organic acid at a concentration of 20 mM to 30 mM, the pH of the second reagent is preferably 5.5 to 6.4, more preferably 5.5 to 6.2. When the second reagent contains the aromatic organic acid at a concentration of 30 mM to 50 mM, preferably 40 mM to 50 mM, the pH of the second reagent is 5.5 to 7.0. Still more preferably, when the second reagent contains the aromatic organic acid at a concentration of 40 mM to 50 mM, the pH of the second reagent is 5.5 to 6.2.

In this embodiment, the aromatic organic acid means an acid having at least one aromatic ring in a molecule or a salt thereof. The aromatic organic acid may include, for example, aromatic carboxylic acids, aromatic sulphonic acids, and the like. In this embodiment, phthalic acid, benzoic acid, salicylic acid, hippuric acid, p-aminobenzenesulfonic acid, benzenesulfonic acid, and salts thereof are suitably used. The second reagent may contain one or two or more types of aromatic organic acids. When the second reagent contains two or more types of aromatic organic acids, the total concentration thereof may be 20 mM to 50 mM.

As the cationic surfactant, a quaternary ammonium salt surfactant or a pyridinium salt surfactant can be used.

The quaternary ammonium salt surfactant may include, for example, surfactants represented by following formula (II) having 9 to 30 carbon atoms in total.

[Formula 2]

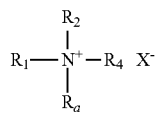

(II)

In formula (II), $R_1$ is an alkyl or alkenyl group having 6 to 18 carbon atoms. $R_2$ and $R_3$ are the same or different from each other and are respectively an alkyl or alkenyl group having 1 to 4 carbon atoms. $R_4$ is an alkyl or alkenyl group having 1 to 4 carbon atoms or a benzyl group. $X^-$ is a halogen atom.

In formula (II), $R_1$ is preferably an alkyl or alkenyl group having 6, 8, 10, 12 or 14 carbon atoms and is particularly preferably a linear alkyl group. More specifically, $R_1$ may include octyl, decyl and dodecyl groups. $R_2$ and $R_3$ are preferably a methyl group, an ethyl group, and a propyl group. $R_4$ is preferably a methyl group, an ethyl group or a propyl group.

The pyridinium salt surfactant may include, for example, surfactants represented by following formula (III).

[Formula 3]

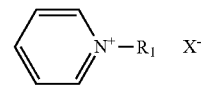

(III)

In formula (III), $R_1$ is an alkyl or alkenyl group having 6 to 18 carbon atoms. $X^-$ is a halogen atom.

In formula (III), $R_1$ is preferably an alkyl or alkenyl group having 6, 8, 10, 12 or 14 carbon atoms and is particularly preferably a linear alkyl group. More specifically, $R_1$ may include octyl, decyl and dodecyl groups.

The concentration of the cationic surfactant in the second reagent may be appropriately adjusted depending on the type of the surfactant and is usually 10 to 10000 ppm, preferably 100 to 1000 ppm.

The nonionic surfactant is preferably a polyoxyethylene nonionic surfactant represented by following formula (VI).

$$R_1—R_2—(CH_2CH_2O)_n—H \qquad (VI)$$

In formula (VI), $R_1$ is an alkyl, alkenyl or alkynyl group having 8 to 25 carbon atoms. $R_2$ is an oxygen atom, —COO— or

[Formula 4]

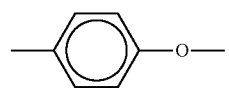

where n is an integer of 10 to 50.

Specific examples of the nonionic surfactant may include polyoxyethylene alkyl ethers, polyoxyethylene sterols, polyoxyethylene castor oils, polyoxyethylene sorbitan fatty acid esters, polyoxyethylene alkylamines, polyoxyethylene polyoxypropylene alkyl ethers, and the like.

The second reagent may usually contain the nonionic surfactant at a concentration of 10 to 100,000 ppm, preferably 100 to 10,000 ppm, more preferably 1,000 to 5,000 ppm.

The second reagent may contain a buffering agent in order to maintain a constant pH. The buffering agent may include, for example, citrate, HEPES, phosphate, and the like. The aromatic organic acid may exhibit a buffering effect in some cases. When such an aromatic organic acid is used, a buffering agent may be optionally added to the second reagent.

The osmotic pressure of the second reagent is not particularly limited, and is preferably 20 to 150 mOsm/kg in order to effectively hemolyze red blood cells.

The second reagent can be obtained by dissolving the surfactants, the aromatic organic acid or a salt thereof and optionally the buffering agent to a suitable solvent so as to obtain the concentration of the aromatic organic acid described above and adjusting pH thereof with NaOH, HCl, and the like. The solvent is not particularly limited as long as the solvent can dissolve the above components, and may include, for example, water, organic solvents, and mixtures thereof. The organic solvents may include, for example, alcohol, methanol, ethylene glycol, DMSO, and the like.

The second reagent may be a commercial hemolytic reagent for classifying white blood cells. Such a hemolytic reagent may include, for example, Lysercell (registered trademark) WDF manufactured by Sysmex Corporation. Lysercell WDF is a hemolytic reagent containing the cationic surfactant and nonionic surfactant described above.

The second reagent configured as described above hemolyzes red blood cells, thereby damaging cell membranes of cells to the extent that the fluorescent dye in the first reagent can permeate the cell membranes of the cells. The first reagent configured as described above stains the cells having the cell membranes damaged by the second reagent.

[Cell Analyzing Method]

Next, description is given of a method of detecting tumor cells in a body fluid sample by using the cell analyzer having the configuration described above.

It is based on the knowledge that there is a correlation between the types of tumor cells and distribution regions in distribution maps (scattergrams) of these tumor cells. Regions where different types of tumor cells are specifically distributed are set in the scattergrams, and the number of cells belonging to each of the regions is counted, thereby detecting the tumor cells in the body fluid based on the counted number of cells.

In this embodiment, the tumor cells include aggregated tumor cells, in which cells are aggregated, and non-aggregated tumor cell, in which cells are not aggregated. In view of this, the aggregated tumor cells and the non-aggregated tumor cells are considered to be different types of tumor cells. The aggregated tumor cells and the non-aggregated tumor cells are specifically distributed in specific regions.

The aggregated tumor cells are larger than nucleated cells including white blood cells, macrophages, and mesothelial cells, and are specifically distributed in an "aggregated cell detection region" in the scattergram. Therefore, the aggregated tumor cells in the body fluid can be identified and detected from other cells in the body fluid by counting the number of cells belonging to the aggregated cell detection region. For example, in a scattergram using forward scattered light signal intensity and forward scattered light signal width, a region having a forward scattered light signal width larger than that of a region where non-aggregated particles are distributed can be set as the aggregated cell detection region.

On the other hand, the non-aggregated tumor cells are specifically distributed in a "non-aggregated cell detection region" in the scattergram, which is located between a white blood cell distribution region and a mesothelial cell distribution region in terms of the fluorescent signal intensity. Therefore, the non-aggregated tumor cells in the body fluid can be identified and detected from the other cells in the body fluid by counting the number of cells belonging to the non-aggregated cell detection region. For example, in a scattergram using fluorescent signal intensity and forward scattered light signal intensity, a region having fluorescent signal intensity larger than that of a region where white blood cells are distributed and smaller than that of a region where mesothelial cells are distributed can be set as the non-aggregated cell detection region.

The aggregated cell detection region, the non-aggregated cell detection region, and also a region where nucleated cells such as macrophages are distributed in the scattergram can be obtained as follows, for example. Specifically, percentages (%) of the aggregated tumor cells, macrophages, and the like in the body fluid are obtained by visually observing a smear of cells with a microscope. Then, it is specified, based on the percentage information, what is distributed in a certain region in the scattergram. For example, when the percentage of macrophages in the body fluid is 30%, a region where 30% of the total number of macrophages are collectively distributed in the scattergram is estimated as the distribution of macrophages. By performing this operation on multiple samples, it can be specified in which region on the scattergram certain nucleated cells are distributed.

Figure 5A:
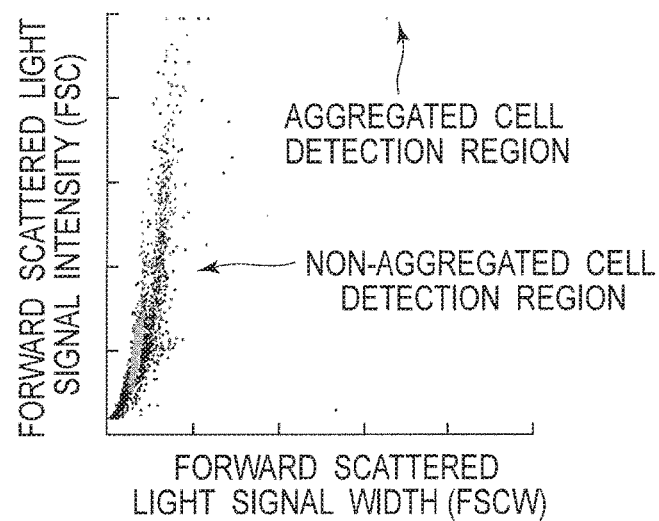
FIGS. 5A and 5B are diagrams illustrating an example of scattergrams of a negative sample.
Figure 5B:
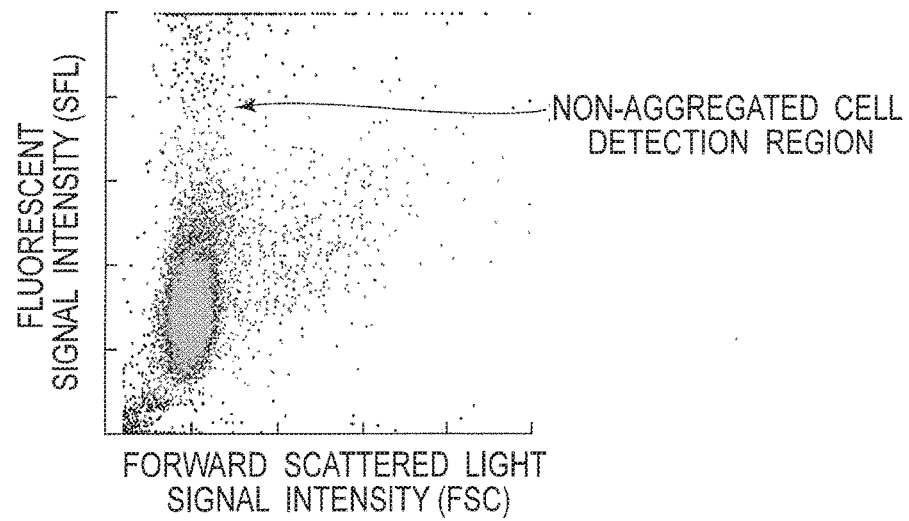
Figure 6A:
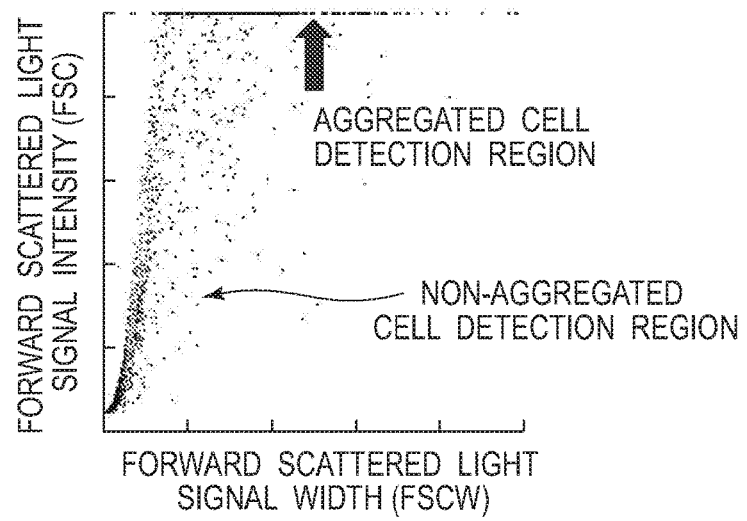
FIGS. 6A and 6B are diagrams illustrating an example of scattergrams in which aggregated tumor cells are detected in an aggregated cell detection region.

FIGS. 5A and 5B illustrate an example of scattergrams of a negative sample containing no tumor cells. In FIGS. 5A and 5B as well as FIGS. 6A, 6B, 7A, and 7B to be described later, FIGS. 5A, 6A, and 7A illustrate scattergrams with forward scattered light signal intensity (FSC) as the vertical axis and forward scattered light signal width (FSCW) as the horizontal axis. On the other hand, FIGS. 5B, 6B, and 7B illustrate scattergrams with fluorescent signal intensity (SFL) as the vertical axis and forward scattered light signal intensity (FSC) as the horizontal axis.

In the negative sample, the percentage of tumor cells is 0.00% and the percentage of mesothelial cells is 21.21%. Note that "%" represents the percentage to the number of white blood cells. The fact that the percentage of mesothelial cells is 21.21% means that the number of mesothelial cells contained per 100 white blood cells is 21.21.

From the negative sample, no tumor cells are detected in either the aggregated cell detection region or the non-aggregated cell detection region.

Figure 6B:
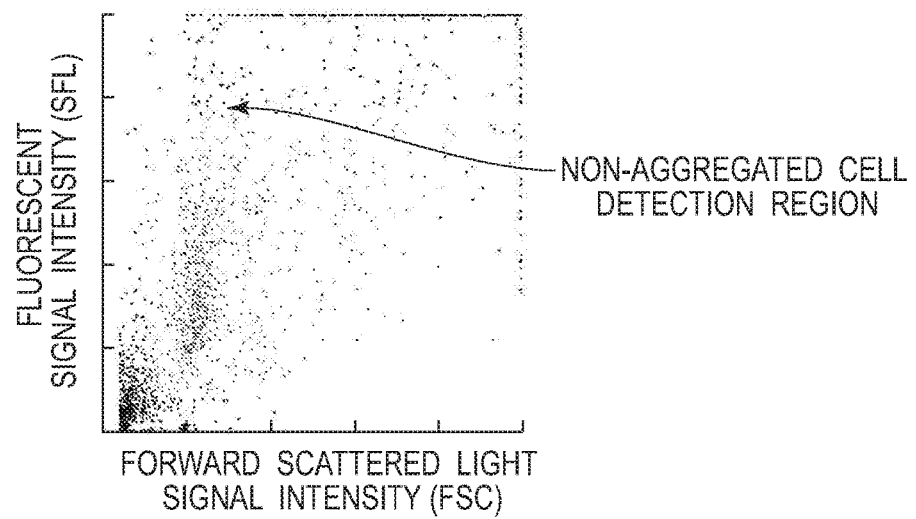
Figure 7A:
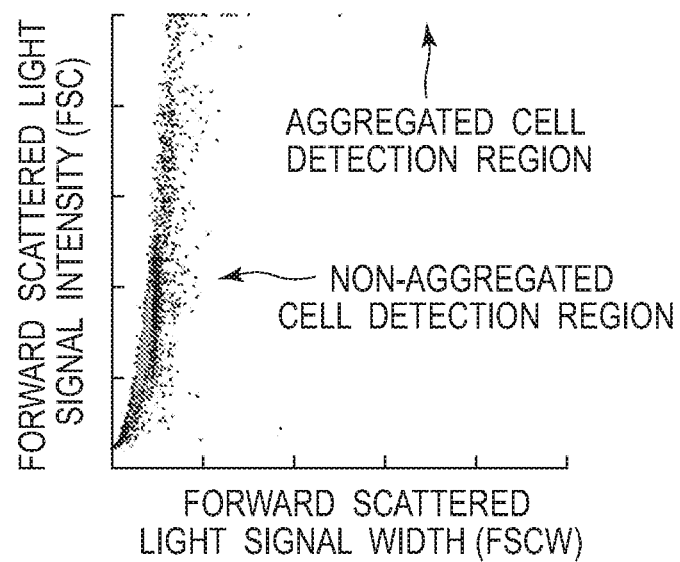
FIGS. 7A and 7B are diagrams illustrating an example of scattergrams in which non-aggregated tumor cells are detected in a non-aggregated cell detection region.
Figure 7B:
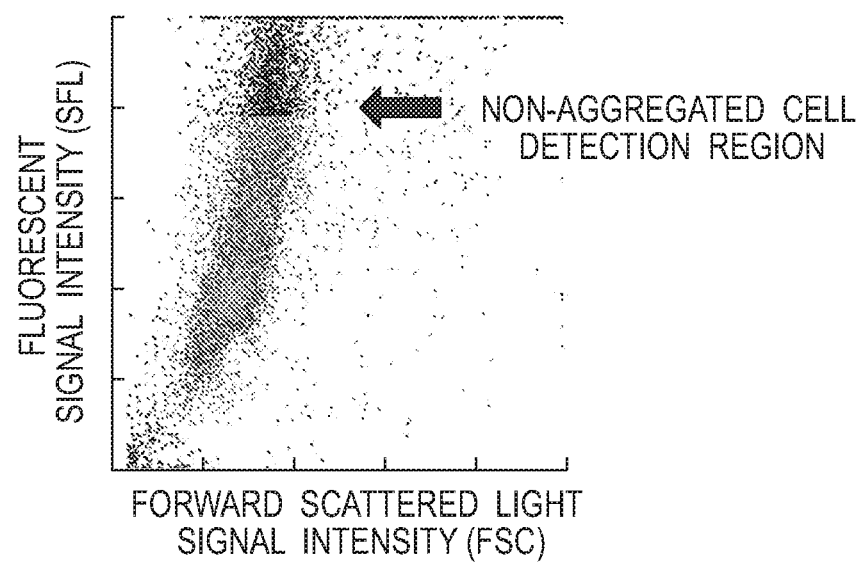

FIGS. 6A and 6B illustrate an example of scattergrams of a sample containing aggregated tumor cells. In this sample, the percentage of tumor cells is 66.2% and the percentage of mesothelial cells is 13.14%.

From this sample, the aggregated tumor cells are detected in the aggregated cell detection region indicated by the thick black arrow in FIG. 6A.

FIGS. 7A and 7B illustrate an example of scattergrams of a sample containing non-aggregated tumor cells. In this sample, the percentage of tumor cells is 662.0% and the percentage of mesothelial cells is 8.00%.

From this sample, the non-aggregated tumor cells are detected in the non-aggregated cell detection region indicated by the thick black arrow in FIG. 7B.

First Embodiment

FIG. 8 is a flowchart illustrating processing by measurement unit 2 and information processing unit 4 in a cell analyzing method according to a first embodiment. In the first embodiment, aggregated tumor cells can be detected among tumor cells. The aggregated tumor cells are larger than nucleated cells including white blood cells, macrophages, and mesothelial cells, and are specifically distributed in a region (aggregated cell detection region) where the forward scattered light signal width is larger than that in the region where non-aggregated particles are distributed in a scattergram using forward scattered light signal intensity and forward scattered light signal width. The aggregated tumor cells are detected among the tumor cells by utilizing the specific distribution in the region described above.

First, in Step S1, measurement unit 2 performs preparation processing of a measurement specimen in order to hemolyze red blood cells contained in a body fluid sample and fluorescently stain nucleic acid of nucleated cells. To be more specific, as described above, the measurement specimen is prepared by mixing a body fluid sample collected from a patient, a first reagent, and a second reagent and heating the mixed liquid with heater H.

Then, in Step S2, measurement unit 2 performs cell detection processing based on the measurement specimen prepared in Step S1. To be more specific, a forward scattered light signal, a side scattered light signal, and a fluorescent signal for each cell are acquired by optical detector D as described above.

In Step S3, the signals acquired by measurement unit 2 are transmitted to information processing unit 4.

In Step S11, CPU 401 in information processing unit 4 receives the forward scattered light signal, side scattered light signal, and fluorescent signal for each cell from measurement unit 2, and stores the received signals in hard disk 404.

Then, in Step S12, CPU 401 creates a first scattergram based on the received signals. The first scattergram is a scattergram with forward scattered light signal intensity (FSC) as the vertical axis and forward scattered light signal width (FSCW) as the horizontal axis.

Figure 9:
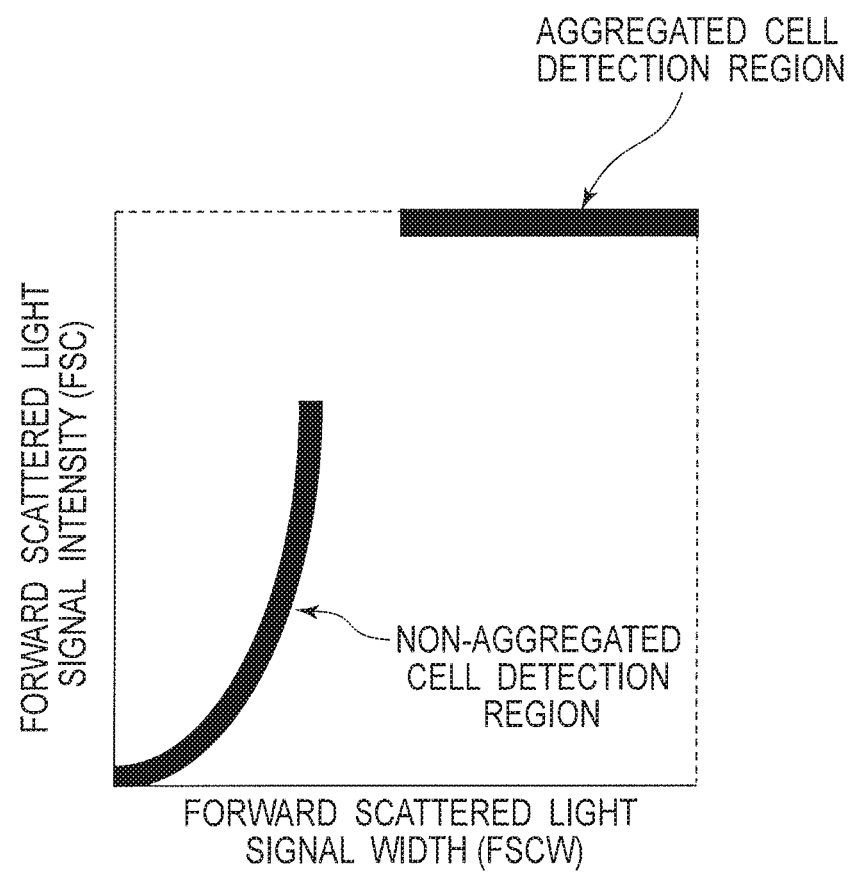
FIG. 9 is a schematic view of a scattergram used in the cell analyzing method according to the first embodiment.

FIG. 9 is a schematic view of the created first scattergram. The aggregated tumor cells are larger than nucleated cells including white blood cells, macrophages, and mesothelial cells, and thus are specifically distributed in the region (aggregated cell detection region) where the forward scattered light signal intensity and forward scattered light signal width are larger than those in the region (non-aggregated cell detection region) where non-aggregated particles such as white blood cells are distributed, as described above. Note that large particles whose forward scattered light signal intensity is a predetermined value or more and which scale out of the scattergram are displayed at the position of highest intensity on the scattergram.

Then, in Step S13, CPU 401 counts the number of cells C1 distributed in the aggregated cell detection region.

Thereafter, in Step S14, CPU 401 determines whether or not the number of cells C1 counted in Step S13 is not less than predetermined value T1. When it is determined that the number of cells C1 is not less than predetermined value T1 (YES), the processing advances to Step S15 where CPU 401 sets a value of a determination flag to 1, which is stored in RAM 403 or hard disk 404. On the other hand, when it is determined that the number of cells C1 is less than predetermined value T1 (NO), CPU 401 advances the processing to Step S16.

In Step S16, CPU 401 displays an analysis result screen on output unit 41. The analysis result screen can display, for example, sample numbers, research items, the created first scattergram, alerts to be described later, and the like.

Then, in Step S16, CPU 401 determines whether or not the value of the determination flag is 1. When it is determined that the value of the determination flag is 1 (YES), the processing advances to Step S18. In Step S18, CPU 401 displays an alert to the effect that the measured body fluid sample may contain aggregated tumor cells on the analysis result screen of output unit 41. On the other hand, when it is determined that the value of the determination flag is not 1 (NO), the processing is terminated.

Second Embodiment

FIG. 10 is a flowchart illustrating processing by measurement unit 2 and information processing unit 4 in a cell analyzing method according to a second embodiment. In the second embodiment, non-aggregated tumor cells can be detected among tumor cells. The non-aggregated tumor cells appear across regions where mononuclear white blood cells and mesothelial cells appear in a scattergram using fluorescent signal intensity and forward scattered light signal intensity. However, the non-aggregated tumor cells exhibit specific distribution in a region (non-aggregated cell detection region) where the fluorescent signal intensity is larger than that in the region where the mononuclear white blood cells are distributed and smaller than that in the region where the mesothelial cells are distributed. The non-aggregated tumor cells are detected among the tumor cells by utilizing the specific distribution in the region described above. With this method, the non-aggregated tumor cells cannot be detected when the non-aggregated tumor cells appear only in the regions where the mononuclear white blood cells and the mesothelial cells appear. However, the non-aggregated tumor cells appear across the regions where the mononuclear white blood cells and the mesothelial cells appear around the non-aggregated cell detection region. Therefore, the appearance of the non-aggregated tumor cells in the body fluid sample can be detected with a high specificity by counting the number of cells appearing in the non-aggregated cell detection region.

Preparation processing (Step S1) for a measurement specimen by measurement unit 2, cell detection processing (Step S2), and transmission (Step S3) of acquired signals to information processing unit 4 are the same as Steps S1 to S3 in the first embodiment. Therefore, description thereof is omitted to facilitate explanation.

In Step S21, CPU 401 in information processing unit 4 receives a forward scattered light signal, a side scattered light signal, and a fluorescent signal for each cell from measurement unit 2, and stores the received signals in hard disk 404.

In Step S22, CPU 401 creates a second scattergram based on the received signals. The second scattergram is a scattergram with fluorescent signal intensity (SFL) as the vertical axis and forward scattered light signal intensity (FSC) as the horizontal axis.

FIG. 11 is a schematic view of the created second scattergram. In a scattergram with side fluorescence intensity (SFL) as the vertical axis and forward scattered light signal intensity (FSC) as the horizontal axis, the non-aggregated tumor cells are specifically distributed in the region (non-aggregated cell detection region) where the fluorescent signal intensity is larger than that in the region where white blood cells are distributed and smaller than that in the region where mesothelial cells are distributed.

In Step S23, CPU 401 counts the number of cells C2 distributed in the non-aggregated cell detection region. By setting the non-aggregated cell detection region as described above, the non-aggregated tumor cells can be counted separately from at least white blood cells, macrophages, and mesothelial cells, as illustrated in FIG. 11, based on the second scattergram created from optical information such as the detected fluorescent signals.

In Step S24, CPU 401 determines whether or not the number of cells C2 counted in Step S23 is not less than predetermined value T2. When it is determined that the number of cells C2 is not less than predetermined value T2 (YES), the processing advances to Step S25 where CPU 401 sets a value of a determination flag to 1, which is stored in RAM 403 or hard disk 404. On the other hand, when it is determined that the number of cells C2 is less than predetermined value T2 (NO), CPU 401 advances the processing to Step S26.

In Step S26, CPU 401 displays an analysis result screen on output unit 41. The analysis result screen can display, for example, sample numbers, research items, the created second scattergram, alerts to be described later, and the like.

Then, in Step S26, CPU 401 determines whether or not the value of the determination flag is 1. When it is determined that the value of the determination flag is 1 (YES), the processing advances to Step S28. In Step S28, CPU 401 displays an alert to the effect that the measured body fluid sample may contain non-aggregated tumor cells on the analysis result screen of output unit 41. On the other hand, when it is determined that the value of the determination flag is not 1 (NO), the processing is terminated.

Third Embodiment

FIG. 12 is a flowchart illustrating processing by measurement unit 2 and information processing unit 4 in a cell analyzing method according to a third embodiment. In the third embodiment, aggregated tumor cells and non-aggregated tumor cells can be individually detected among tumor cells. More specifically, the aggregated tumor cells are detected in the same manner as the first embodiment, and the non-aggregated tumor cells are detected in the same manner as the second embodiment. Thus, the cell analyzing method according to the third embodiment can improve detection accuracy for the tumor cells compared with the cell analyzing method according to the first embodiment or the second embodiment. Moreover, contents of alert may be changed according to reliability of analysis, such as issuing an alert (high) with high accuracy when a predetermined number or more of both aggregated tumor cells and non-aggregated tumor cells are detected and issuing an alert (low) with somewhat low accuracy when a predetermined number or more of one of the tumor cells are detected.

Preparation processing (Step S1) for a measurement specimen by measurement unit 2, cell detection processing (Step S2), and transmission (Step S3) of acquired signals to information processing unit 4 are the same as Steps S1 to S3 in the first or second embodiment. Therefore, description thereof is omitted to facilitate explanation.

In Step S31, CPU 401 in information processing unit 4 receives a forward scattered light signal, a side scattered light signal, and a fluorescent signal for each cell from measurement unit 2, and stores the received signals in hard disk 404.

In Step S32, CPU 401 creates a first scattergram based on the received signals. The first scattergram is a scattergram with forward scattered light signal intensity (FSC) as the vertical axis and forward scattered light signal width (FSCW) as the horizontal axis (see FIG. 9).

In Step S33, CPU 401 counts the number of cells C1 distributed in the aggregated cell detection region.

In Step S34, CPU 401 determines whether or not the number of cells C1 counted in Step S33 is not less than predetermined value T1. When it is determined that the number of cells C1 is not less than predetermined value T1 (YES), the processing advances to Step S15 where CPU 401 sets a value of a determination flag to 1, which is stored in RAM 403 or hard disk 404. On the other hand, when it is determined that the number of cells C1 is less than predetermined value T1 (NO), CPU 401 advances the processing to Step S36.

In Step S36, CPU 401 creates a second scattergram based on the received signals. The second scattergram is a scattergram with fluorescent signal intensity (SFL) as the vertical axis and forward scattered light signal intensity (FSC) as the horizontal axis.

In Step S37, CPU 401 counts the number of cells C2 distributed in the non-aggregated cell detection region.

In Step S38, CPU 401 determines whether or not the number of cells C2 counted in Step S37 is not less than predetermined value T2. When it is determined that the number of cells C2 is not less than predetermined value T2 (YES), the processing advances to Step S39. In Step S39, CPU 401 determines whether or not a determination flag is 1. When it is determined that the determination flag is 1 (YES), the processing advances to Step S40. In Step S40, CPU 401 sets a value of the determination flag to 2, which is stored in RAM 403 or hard disk 404. On the other hand, when it is determined that the determination flag is not 1 (NO), CPU 401 advances the processing to Step S41.

In Step S41, CPU 401 displays an analysis result screen on output unit 41. The analysis result screen can display, for example, sample numbers, research items, the created first and second scattergrams, alerts (high) or (low) to be described later, and the like.

In Step S42, CPU 401 determines whether or not the value of the determination flag is 2. When it is determined that the value of the determination flag is 2 (YES), the processing advances to Step S43. In Step S43, CPU 401 displays an alert (high) to the effect that there is a high possibility that the measured body fluid sample contains aggregated tumor cells on the analysis result screen of output unit 41. On the other hand, when it is determined that the value of the determination flag is not 2 (NO), CPU 401 advances the processing to Step S44. In Step S44, CPU 401 determines whether or not the value of the determination flag is 1. When it is determined in Step S44 that the value of the determination flag is 1 (YES), the processing advances to Step S45. In Step S45, CPU 401 displays an alert (low) to the effect that the measured body fluid sample may contain aggregated tumor cells on the analysis result screen of output unit 41. On the other hand, when it is determined that the value of the determination flag is not 1 (NO), the processing is terminated.

In this embodiment, the tumor cells in the body fluid are detected by creating the first scattergram, creating the second scattergram after counting the number of cells C1 in the aggregated cell detection region in the first scattergram, and counting the number of cells C2 in the non-aggregated cell detection region in the second scattergram. Alternatively, the tumor cells in the body fluid can also be detected by creating the second scattergram, creating the first scattergram after counting the number of cells C2 in the non-aggregated cell detection region in the second scattergram, and counting the number of cells C1 in the aggregated cell detection region in the first scattergram.

Moreover, although two types of alerts are issued in this embodiment, only one type of alert may be issued. More specifically, an alert may be issued when at least one of the counted numbers of aggregated tumor cells and non-aggregated tumor cells is a predetermined value or more. In this case, again, it can be accurately detected whether or not the body fluid sample contains tumor cells compared with the case where an alert indicating the presence or absence of tumor cells is issued based on determination of only one of the aggregated tumor cells and non-aggregated tumor cells.

EXAMPLES

Next, description is given of examples of the cell analyzing method according to embodiments. The invention is not limited to such examples.

Example 1

With the cell analyzing method according to the first embodiment, tumor cell detection is performed for 220 samples. The types of samples are cerebrospinal fluid and pleural effusion, and adenocarcinoma considered to be aggregated is set as a target. Fluorocell WDF is used as a first reagent, and Lysercell WDF is used as a second reagent. Table 1 shows a comparison result with visual observation. In Table 1, "1" represents a positive result (with aggregated tumor cells) and "0" represents a negative result (without aggregated tumor cells).

TABLE 1

|     |   | XN  |   |
| --- | --- | --- | --- |
|     |   | 0   | 1 |
| ref | 0 | 207 | 2 |
|     | 1 | 3   | 8 |

In Example 1, the sensitivity is 72.2% and the specificity is 98.0%. A positive predictive value (PPV) is 76.5% and a negative predictive value (NPV) is 98.6%.

Example 2

With the cell analyzing method according to the second embodiment, tumor cell detection is performed for 209 samples. The types of samples are cerebrospinal fluid and pleural effusion, and tumors other than adenocarcinoma are set as a target. Fluorocell WDF is used as a first reagent, and Lysercell WDF is used as a second reagent. Table 2 shows a comparison result with visual observation.

TABLE 2

|     |   | XN  |    |
| --- | --- | --- | --- |
|     |   | 0   | 1  |
| ref | 0 | 191 | 10 |
|     | 1 | 5   | 3  |

In Example 2, the sensitivity is 37.5% and the specificity is 95.0%. A positive predictive value PPV is 23.1% and a negative predictive value NPV is 97.4%.

Example 3

With the cell analyzing method according to the third embodiment, tumor cell detection is performed for 220 samples. The types of samples are cerebrospinal fluid and pleural effusion. Fluorocell WDF is used as a first reagent, and Lysercell WDF is used as a second reagent. Table 3 shows a comparison result with visual observation. A positive result is obtained when a predetermined number or more of at least one of aggregated tumor cells and non-aggregated tumor cells are detected.

TABLE 3

|     |   | XN  |    |
| --- | --- | --- | --- |
|     |   | 0   | 1  |
| ref | 0 | 198 | 4  |
|     | 1 | 5   | 13 |

In Example 3, the sensitivity is 72.2% and the specificity is 98.0%. A positive predictive value PPV is 76.5% and a negative predictive value NPV is 97.5%.

In this way, the cell analyzer and the cell analyzing method according to the embodiments described above can detect tumor cells in a body fluid.

Other Modified Examples

The invention is not limited to the embodiments described above but various modifications can be made thereto within the scope of the claims.

In other words, the invention includes other embodiments in addition to the above-described embodiments without departing from the spirit of the invention. The embodiments are to be considered in all respects as illustrative, and not restrictive. The scope of the invention is indicated by the appended claims rather than by the foregoing description. Hence, all configurations including the meaning and range within equivalent arrangements of the claims are intended to be embraced in the invention.

The invention claimed is:

1. A cell analyzer comprising:
    a flow cell through which a measurement specimen containing a body fluid flows;
    a light emission unit that applies light onto the measurement specimen flowing through the flow cell;
    a light detection unit that detects forward scattered light generated from cells in the measurement specimen to which the light is applied;
    an analysis unit that is programmed to analyze the cells in the body fluid based on a forward scattered light signal detected by the light detection unit; and
    an output unit,
    wherein
    the analysis unit is programmed to control the output unit to output information about tumor cells in the body fluid, based on forward scattered light signal intensity and forward scattered light signal width,
    the analysis unit is programmed to count the number of cells belonging to an aggregated cell detection region where the forward scattered light signal intensity and forward scattered light signal width are larger than those in a white blood cell distribution region, and
    the analysis unit outputs the information about the tumor cells in the body fluid to the output unit, based on information about the counted number of cells belonging to the aggregated cell detection region.

2. The cell analyzer according to claim 1, wherein
    the analysis unit is programmed to count the number of cells belonging to a non-aggregated cell detection region which is located between a white blood cell distribution region and a mesothelial cell distribution region in terms of fluorescent signal intensity, and
    the analysis unit is programmed to control the output unit to output the information about the tumor cells in the body fluid, based on the counted number of cells belonging to the non-aggregated cell detection region.

3. The cell analyzer according to claim 1, further comprising:
a specimen preparation unit that prepares the measurement specimen by hemolyzing red blood cells in the body fluid.

4. The cell analyzer according to claim 3, wherein the specimen preparation unit prepares the measurement specimen by fluorescently staining nucleic acids of nucleated cells in the body fluid.

5. A cell analyzer comprising:
a flow cell through which a measurement specimen containing a body fluid flows;
a light emission unit that applies light onto the measurement specimen flowing through the flow cell;
a light detection unit that detects forward scattered light generated from cells in the measurement specimen to which the light is applied;
an analysis unit that is programmed to analyze the cells in the body fluid based on a forward scattered light signal detected by the light detection unit; and
an output unit,
wherein
the analysis unit is programmed to control the output unit to output information about tumor cells in the body fluid, based on forward scattered light signal intensity and forward scattered light signal width,
the measurement specimen is obtained by fluorescently staining nucleic acids of nucleated cells in the body fluid and flows through the flow cell,
the light detection unit detects fluorescence generated from the cells in the measurement specimen to which the light is applied, and
the analysis unit is programmed to control the output unit to output the information about the tumor cells in the body fluid, based on fluorescent signal intensity and the forward scattered light signal intensity.

6. The cell analyzer according to claim 5, wherein the analysis unit is programmed to count the number of cells belonging to a non-aggregated cell detection region which is located between a white blood cell distribution region and a mesothelial cell distribution region in terms of fluorescent signal intensity, and
the analysis unit is programmed to control the output unit to output the information about the tumor cells in the body fluid, based on the counted number of cells belonging to the non-aggregated cell detection region.

7. The cell analyzer according to claim 5, further comprising:
a specimen preparation unit that prepares the measurement specimen by hemolyzing red blood cells in the body fluid.

8. A cell analyzer comprising:
a flow cell through which a measurement specimen flows, the measurement specimen being obtained by fluorescently staining nucleic acids of nucleated cells in a body fluid;
a light emission unit that applies light onto the measurement specimen flowing through the flow cell;
a light detection unit that detects fluorescence generated from cells in the measurement specimen to which the light is applied;
an analysis unit that is programmed to analyze cells in the body fluid based on fluorescent signal intensity detected by the light detection unit; and
an output unit,
wherein
the analysis unit is programmed to control the output unit to output information about tumor cells in the body fluid, based on the fluorescent signal intensity and forward scattered light signal intensity,
the analysis unit is programmed to count the number of cells belonging to a non-aggregated cell detection region which is located between a white blood cell distribution region and a mesothelial cell distribution region in terms of the fluorescent signal intensity, and
the analysis unit is programmed to control the output unit to output the information about the tumor cells in the body fluid, based on information about the counted number of cells belonging to the non-aggregated cell detection region.

* * * * *